United States Patent
Inomata et al.

(10) Patent No.: US 6,852,897 B2
(45) Date of Patent: Feb. 8, 2005

(54) PROCESS FOR THE PREPARATION OF LOWER OLEFINS

(75) Inventors: Makoto Inomata, Oarai-machi (JP);
Akira Higashi, Yokohama (JP);
Yoshiteru Makino, Yokohama (JP);
Yoshinori Mashiko, Yokohama (JP)

(73) Assignee: JGC Corporation, Tokyo (JP)

( * ) Notice: Subject to any disclaimer, the term of this patent is extended or adjusted under 35 U.S.C. 154(b) by 0 days.

(21) Appl. No.: 10/311,731

(22) PCT Filed: Jun. 12, 2001

(86) PCT No.: PCT/JP01/04970
§ 371 (c)(1),
(2), (4) Date: Dec. 18, 2002

(87) PCT Pub. No.: WO01/98237
PCT Pub. Date: Dec. 27, 2001

(65) Prior Publication Data
US 2003/0149319 A1 Aug. 7, 2003

(30) Foreign Application Priority Data
Jun. 23, 2000 (JP) .................................... 2000-189573

(51) Int. Cl.[7] .............................. C07C 1/04; C07C 1/207
(52) U.S. Cl. ........................ 585/327; 585/639; 585/640
(58) Field of Search ................................ 585/634, 640, 585/327

(56) References Cited

U.S. PATENT DOCUMENTS 5,177,114 A * 1/1993 Van Dijk et al. ........... 518/703
5,714,662 A    2/1998 Vora et al.

FOREIGN PATENT DOCUMENTS

| EP | 187594 A2 | 7/1986 |
|----|-----------|--------|
| EP | 289233 A1 | 11/1988 |
| EP | 318282 A2 | 5/1989 |
| JP | (1985) 60-126233 A | 7/1985 |
| JP | (1987) 62-70324 A | 3/1987 |
| JP | (1987) 62-70325 A | 3/1987 |
| JP | (1992) 4-217928 A | 8/1992 |
| JP | (1998) 10-259148 A | 9/1998 |
| WO | WO 99/55651 A1 | 11/1999 |

* cited by examiner

Primary Examiner—Thuan Dinh Dang
(74) Attorney, Agent, or Firm—Webb Ziesenheim Logsdon Orkin & Hanson, P.C.

(57) ABSTRACT

A process for the preparation of lower olefins which comprises the step (A) of separating in a high-pressure state a mixed fluid (I) containing dimethyl ether (DME) and methanol at a specified ratio into a gas component (II) and a liquid component (III), separating the gas component (II) into an off-gas and DME, and then making this DME join the liquid component (III) to obtain a liquid component (IV) containing DME and methanol at a specified ratio and the step (B) of subjecting the liquid component (IV) to depressurization and then introducing it into a reactor for the preparation of olefins to form a lower olefin fraction (V). Lower olefins are prepared from a mixed fluid (I) containing DME and methanol at a specified ratio.

15 Claims, 1 Drawing Sheet

PROCESS FOR THE PREPARATION OF LOWER OLEFINS

BACKGROUND OF THE INVENTION

1. Field of the Invention

The present invention relates to a process for producing lower olefins (light olefins) from a mixture containing dimethyl ether and methanol. More particularly, the invention relates to a process for producing lower olefins from a mixture containing carbon monoxide and hydrogen and further containing dimethyl ether and methanol in a specific ratio, with high energy efficiency.

2. Description of the Prior Art

In recent years, a demand for propylene has been greater in the market than that for ethylene, and hence the development of a process for producing lower olefins in a high yield of propylene at a low production cost has been desired.

Lower olefins such as ethylene and propylene are industrially produced mainly by thermal cracking using ethane or naphtha as a starting material. In the process for producing lower olefins by an ethane cracker using ethane as a starting material, a major component of the resulting lower olefins is ethylene and the content of propylene is very low, so that production of propylene by this process is not practical.

In the lower olefins obtained by a naphtha cracker using naphtha as a starting material, the propylene content is higher than that in the lower olefins produced by the ethane cracker, but they still do not agree with the demand-supply balance of ethylene/propylene in the market.

Further, production of lower olefins by the ethane cracker or the naphtha cracker has a problem of high energy cost because high-temperature thermal cracking at about 800 to 1,000° C. is generally carried out.

Moreover, production of lower olefins using a petroleum type starting material such as naphtha is not economical because the material is expensive. In addition, by-products such as methane and hydrogen are formed in large amounts, and separation of the by-products needs great energy. Therefore, a process for producing lower olefins such as ethylene and propylene from a starting material other than the petroleum type starting material such as naphtha has been desired.

The process using no petroleum type starting material is, for example, a process for producing lower olefins from methanol. In this process, generally, a mixture containing methanol (crude methanol) is formed from a synthesis gas, then high-purity methanol is isolated from the mixture by distillation or the like, and the resulting methanol is allowed to undergo reaction at an intermediate temperature such as a temperature of about 300 to 600° C. to produce lower olefins. According to this process, lower olefins can be obtained in a higher yield of propylene than that in the process using the ethane cracker or the naphtha cracker, and the ratio between ethylene and propylene can be flexibly controlled.

In such a conventional process for producing lower olefins from methanol as described above, however, methanol having higher purity than the mixture is isolated and used, so that there resides a problem of high equipment cost and high energy cost related to the isolation of methanol.

Under the above circumstances, there has been proposed a process for producing lower olefins in which crude methanol is formed from a synthesis gas and this crude methanol is used without being purified (U.S. Pat. No. 5,714,662). According to this process, a mixture containing methanol and a small amount of dimethyl ether (sometimes referred to as "DME" hereinafter) produced as a by-product is formed from a synthesis gas, and this mixture is used as a starting material for the olefin production to produce $C_2$–$C_4$ olefins. In this process, further, the resulting butene fraction is converted into an ether of high octane value and used.

Under such circumstances as mentioned above, the present inventors have earnestly studied a process for producing lower olefins more efficiently, and as a result, they have found that lower olefins containing ethylene and propylene in a desired ratio can be produced with particularly high energy efficiency by converting a mixed fluid containing DME and methanol in a specific weight ratio into lower olefins. Based on the finding, the present invention has been accomplished.

It is an object of the present invention to provide a process for producing lower olefins, by which lower olefins containing ethylene and propylene can be produced from a mixed fluid containing carbon monoxide and hydrogen and further containing DME and methanol with high energy efficiency.

SUMMARY OF THE INVENTION

The process for producing lower olefins according to the invention comprises:

(A) a step wherein a mixed fluid (I) containing carbon monoxide and hydrogen and further containing dimethyl ether and methanol in a dimethyl ether/methanol weight ratio of 25/75 to 95/5 is separated into a gas component (II) and a liquid component (III) by a high-pressure gas-liquid separation means under high pressure, then the gas component (II) is separated into an off-gas and dimethyl ether, and the separated dimethyl ether is allowed to join the liquid component (III) to obtain a liquid component (IV) having a dimethyl ether/methanol weight ratio of 30/70 to 90/10, and (B) a step wherein the pressure of the liquid component (IV) is released, and then the liquid component (IV) is introduced into an olefin production means to produce a lower olefin fraction (V) containing ethylene and propylene.

In the process for producing lower olefins according to the invention, the mixed fluid (I) is preferably a mixed fluid obtained when a gaseous mixture containing carbon monoxide and hydrogen is introduced into an oxygen-containing compound synthesis means to allow carbon monoxide and hydrogen to react with each other and thereby synthesize methanol, and from the methanol, dimethyl ether and water are formed. A part of the gas component (II) is preferably introduced into the oxygen-containing compound synthesis means as a recycle gas, together with the gaseous mixture containing carbon monoxide and hydrogen. The gaseous mixture containing carbon monoxide and hydrogen is preferably a synthesis gas obtained from natural gas.

The process for producing lower olefins according to the invention preferably further comprises a step of fractionating the lower olefin fraction (V) into an ethylene fraction, a propylene fraction and a butene fraction by fractional distillation. It is preferable to use the off-gas as a gas turbine fuel. In the step (B), it is preferable to recover energy generated by the pressure release. It is also preferable to use, as a power of a compressor, the energy generated by the pressure release and recovered.

In the process for producing lower olefins according to the invention, the dimethyl ether/methanol weight ratio in the liquid component (IV) is preferably in the range of 40/60 to 80/20, and the catalyst used in the olefin production reactor is preferably selected from the group consisting of SAPO-34, MFI and MFI type zeolite having been subjected to metallic ion exchange or substitution. The catalyst is also preferably a MFI type zeolite catalyst having been subjected to metallic ion exchange with Ca ion or Zn ion.

In the process for producing lower olefins according to the invention, it is preferable to periodically or continuously regenerate the catalyst and to use it in the olefin production means. The separation of the gas component (II) into an off-gas and dimethyl ether in the step (A) is preferably any one selected from gas-liquid separation by cooling at a temperature of −60 to −20° C., separation using an inorganic membrane and separation using an organic membrane.

BRIEF DESCRIPTION OF THE DRAWING

In FIG. 1, the following numerals are used to identify the associated elements listed below.

Figure 1:
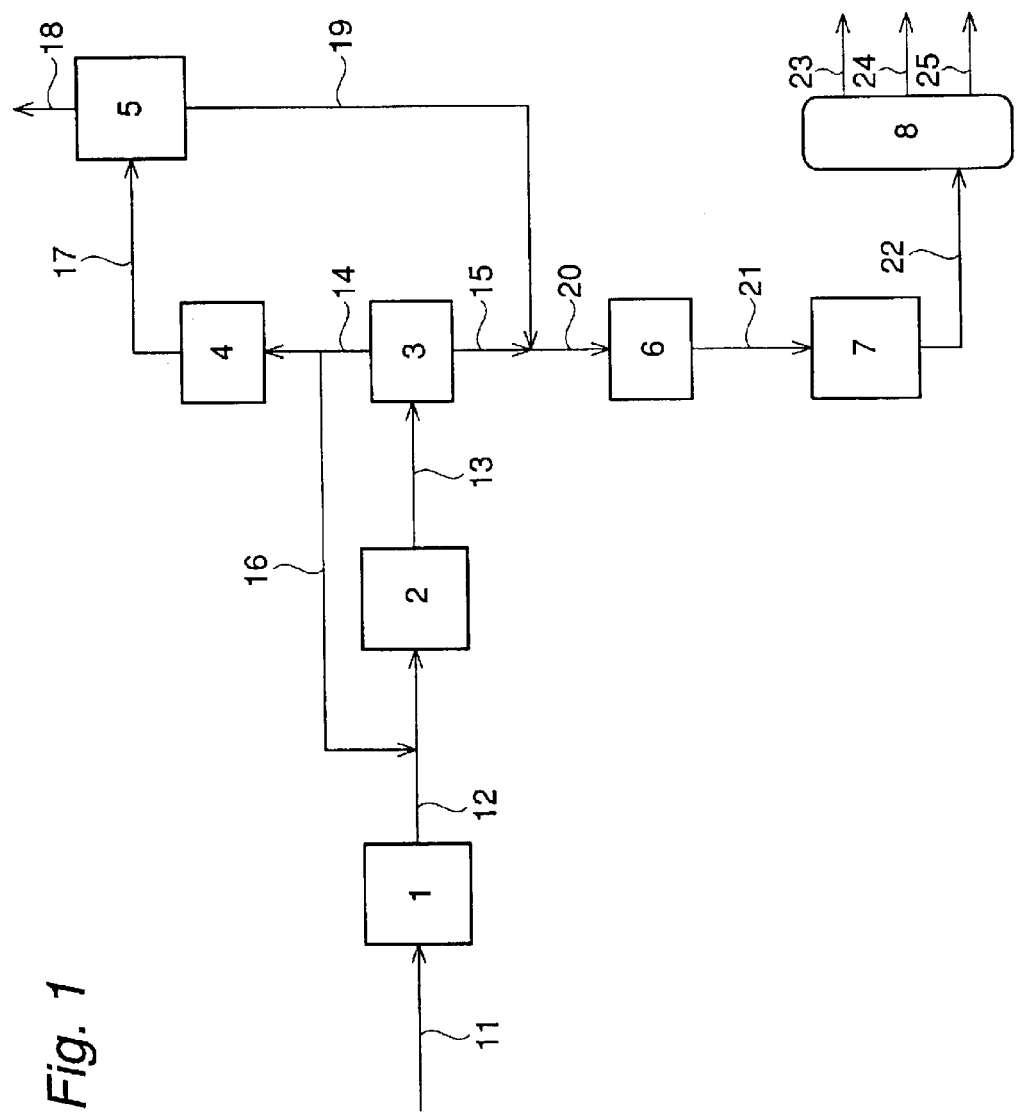
FIG. 1 is a schematic view showing the process steps of Example 1, which represents one embodiment of the present invention.

1: synthesis gas production means
2: oxygen-containing compound synthesis means
3: high-pressure gas-liquid separation means
4: condenser
5: gas-liquid separator
6: expander
7: olefin production means
8: fractional distillation means
11–25: line

DETAILED DESCRIPTION OF THE PREFERRED EMBODIMENTS

The present invention is described in detail hereinafter.

First, the step (A) is described. In this step, a mixed fluid (I) containing carbon monoxide and hydrogen and further containing dimethyl ether and methanol in a dimethyl ether/methanol weight ratio of 25/75 to 95/5 is separated into a gas component (II) and a liquid component (III) by a high-pressure gas-liquid separation means under high pressure, then the gas component (II) is separated into an off-gas and dimethyl ether, and the separated dimethyl ether is allowed to join the liquid component (III) to obtain a liquid component (IV) having a dimethyl ether/methanol weight ratio of 30/70 to 90/10.

The mixed fluid (I) for use in the step (A) of the invention contains carbon monoxide, hydrogen, methanol and dimethyl ether, and the dimethyl ether/methanol weight ratio is in the range of 25/75 to 95/5.

The mixed fluid (I) is, for example, a mixed fluid obtained when a gaseous mixture containing carbon monoxide and hydrogen is introduced into an oxygen-containing compound synthesis means to allow carbon monoxide and hydrogen to react with each other and thereby synthesize methanol, and from the methanol, dimethyl ether and water are formed. The mixed fluid obtained by such a reaction contains unreacted carbon monoxide and hydrogen and also contains dimethyl ether and methanol formed by the reaction.

Examples of the gaseous mixtures containing carbon monoxide and hydrogen include synthesis gases obtained from natural gas, coal, petroleum fraction, recycled plastic and other organic materials. Of these, a synthesis gas obtained from natural gas is preferably employed. The synthesis gas usually contains not only carbon monoxide and hydrogen but also carbon dioxide.

As a method for producing the synthesis gas, any of hitherto known methods is adoptable. For example, there can be mentioned a method in which a starting material such as natural gas is brought into contact with water vapor or a mixed gas of water vapor and oxygen at a high temperature, e.g. a steam reforming method, a method using a synthesis gas production unit of autothermal type.

The volume ratio ($CO/H_2$) of carbon monoxide to hydrogen in the gaseous mixture such as a synthesis gas, which is preferably employable as a starting material for the mixed fluid (I), is as follows. When the gaseous mixture is a synthesis gas obtained from natural gas, the $CO/H_2$ volume ratio is in the range of about 1.5 to 3, and when the gaseous mixture is a synthesis gas obtained from coal, the $CO/H_2$ volume ratio is in the range of about 0.5 to 1.5.

One embodiment of the present invention is described below with reference to FIG. 1.

A starting material such as natural gas is introduced into a synthesis gas production means (1) through a line (11) and allowed to undergo reaction to obtain a gaseous mixture (synthesis gas) containing carbon monoxide and hydrogen. The thus obtained gaseous mixture usually contains not only carbon monoxide and hydrogen but also carbon dioxide. The gaseous mixture is then introduced into an oxygen-containing compound synthesis means (2) through a line (12) together with the later-described recycle gas obtained through a line (16) to allow carbon monoxide and hydrogen contained in the gaseous mixture and the recycle gas to react with each other, whereby a mixed fluid (I) is obtained.

In the oxygen-containing compound synthesis means (2), methanol and dimethyl ether (DME) are formed from carbon monoxide, hydrogen and occasionally carbon dioxide, mainly through the following reaction.

$$CO+2H_2 \rightarrow CH_3OH$$

$$(CO_2+3H_2 \rightarrow CH_3OH+H_2O)$$

$$2CH_3OH \rightarrow CH_3OCH_3+H_2O$$

$$CO+H_2O \rightarrow CO_2+H_2$$

Examples of the catalysts employable in the oxygen-containing compound synthesis means (2) include catalysts for synthesizing methanol, such as CuO—ZnO catalyst, ZnO—$Cr_2O_3$ catalyst and CuO—ZnO—$Cr_2O_3$ catalyst; acid catalysts, such as γ-alumina, silica alumina, phosphoric acid and zeolite; bifunctional catalysts; and mixtures of these catalysts.

The pressure in the oxygen-containing compound synthesis means (2) is desired to be in the range of usually 30 to 150 kg/cm$^2$-G. The gaseous mixture such as a synthesis gas can be appropriately pressurized by a compressor (not shown) equipped on the line (12) and then introduced into the oxygen-containing compound synthesis means (2). The reaction conditions in the oxygen-containing compound synthesis means (2) vary depending upon the ratio between carbon monoxide and hydrogen contained in the gaseous mixture, the type of the catalyst, the type of the reactor, the reaction time, etc., but appropriately selectable are such reaction conditions that the weight ratio of the resulting methanol to the resulting DME becomes a desired one.

When the gaseous mixture is a synthesis gas obtained from natural gas, an oxygen-containing compound synthesis means for conducting gas phase reaction or liquid phase reaction can be preferably employed, and using a mixed catalyst consisting of a methanol synthesis catalyst and an acid catalyst, the oxygen-containing compound synthesis reaction is conducted under the conditions of a temperature of about 210 to 300° C. and a pressure of about 30 to 150 kg/cm$^2$-G, whereby a mixed fluid (I) having a DME/methanol weight ratio of about 25/75 to 95/5 can be obtained.

When the gaseous mixture is a synthesis gas obtained from coal, an oxygen-containing compound synthesis means for conducting liquid phase reaction can be preferably employed, and using a mixed catalyst consisting of a methanol synthesis catalyst and an acid catalyst, the oxygen-containing compound synthesis reaction is conducted under the conditions of a temperature of about 260 to 300° C. and a pressure of about 30 to 90 kg/cm$^2$-G, preferably about 30 to 60 kg/cm$^2$-G, whereby a mixed fluid (I) having a DME/methanol weight ratio of about 25/75 to 95/5 can be obtained.

The mixed fluid (I) is obtained through a line (13) from the oxygen-containing compound synthesis means (2). The mixed fluid (I) contains methanol, DME and water formed by the above reaction and further contains unreacted carbon monoxide, hydrogen and carbon dioxide. In the present invention, the weight ratio (DME/methanol) of DME to methanol contained in the mixed fluid (I) is desired to be in the range of 25/75 to 95/5, preferably 35/65 to 90/10. When the DME/methanol ratio is less than 25/75, predominance of a thermodynamical equilibrium in the dehydration reaction of methanol can not be exerted. When the DME/methanol ratio is more than 95/5, the burden on the catalyst becomes too heavy and the side reaction increases, so that the life of the catalyst may be shortened.

The reaction to form a mixed fluid (I) containing DME and methanol in a specific ratio from the gaseous mixture such as a synthesis gas is of greater advantage to the products from the viewpoint of thermodynamical equilibrium as compared with the reaction to form only methanol as an intermediate target product. On this account, the reaction for the synthesis of the oxygen-containing compound to form DME and methanol in the process of the invention can be sufficiently carried out under milder conditions such as lower pressure conditions than the synthesis reaction to form only methanol as an intermediate target product. In the present invention, therefore, the oxygen-containing compound synthesis means (2) can be designed as a low-pressure type, and the single-pass conversion ratio can be increased. As a result, the energy cost and the equipment cost can be more greatly reduced as compared with the process in which the synthesis reaction to form only methanol as an intermediate target product is carried out.

In the present invention, the mixed fluid (I) is separated into a gas component (II) and a liquid component (III) by a high-pressure gas-liquid separation means under high pressure, then the gas component (II) is separated into an off-gas and dimethyl ether, and the separated dimethyl ether is allowed to join the liquid component (III) to obtain a liquid component (IV) having a dimethyl ether/methanol weight ratio of 30/70 to 90/10.

It is desirable that the mixed fluid (I) is introduced into a high-pressure gas-liquid separation means (3) through a line (13) and subjected to gas-liquid separation under high pressure such as a pressure of usually about 30 to 150 kg/cm$^2$-G. It is also desirable that the mixed fluid (I) is cooled to a temperature of usually about 20 to 50° C., preferably about 35 to 40° C., followed by introduction into the high-pressure gas-liquid separation means (3). The pressure for the high-pressure gas-liquid separation is desired to be equal to the reaction pressure in the oxygen-containing compound synthesis means (2), because the energy required for the compressor is small and economical. In the high-pressure gas-liquid separation means (3), the mixed fluid (I) is separated into the gas component (II) and the liquid component (III), and the gas component (II) and the liquid component (III) are obtained through a line (14) and a line (15), respectively.

In general, the gas component (II) obtained through the line (14) mainly contains unreacted carbon monoxide and hydrogen which were originally contained in the mixed fluid (I), a part of DME and carbon dioxide. It is preferable to return a part of the gas component (II) into the line (12) through a line (16) and to introduce it again into the oxygen-containing compound synthesis means (2) as a recycle gas. The residue of the gas component (II) is cooled to a temperature of usually −60 to −20° C., preferably −40 to −30° C., by a condenser (4) and then subjected to gas-liquid separation using a gas-liquid separator (5) to separate it into an off-gas and DME which are obtained through a line (18) and a line (19), respectively.

The DME obtained through the line (19) is allowed to join the liquid component (III), which contains methanol, DME and water and is obtained through the line (15), to obtain a liquid component (IV) having a dimethyl ether/methanol weight ratio of 30/70 to 90/10 present in a line (20). The liquid component (IV) is finally used as a starting material for producing lower olefin.

The off-gas obtained through the line (18) usually contains unreacted carbon monoxide, hydrogen and carbon dioxide. The off-gas is appropriately employable as a fuel gas, and is particularly preferably employable as a gas turbine fuel.

In order to separate the residue of the gas component (II) into the off-gas and DME, gas-liquid separation by cooling at a temperature of −60 to −20° C. is used as described above. In addition, it is also preferable to separate it by a separator using an inorganic or organic membrane having selective permeability or impermeability to DME contained in the component (II).

Next, the step (B) is described. In this step, the pressure of the liquid component (IV) containing DME and methanol in a specific ratio is released, and then the liquid component (IV) is introduced into an olefin production means to produce a lower olefin fraction (V) containing ethylene and propylene.

The liquid component (IV) containing methanol, DME and water, said liquid component (IV) being present in the line (20), is heated to a temperature of usually 350 to 390° C. and introduced into an expander (6) in which the pressure is released to usually about 3 to 8 kg/cm$^2$-G. In the expander (6), it is desirable to recover energy generated by the pressure release, and the pressure release energy thus recovered is desired to be used as a power of a compressor.

The component (IV) having been subjected to pressure release is further heated to a temperature of usually 300 to 700° C., preferably 350 to 600° C., in a line (21) and then introduced into an olefin production means (7).

In the olefin production means (7), a lower olefin fraction (V) containing ethylene and propylene is produced from the component (IV) containing methanol and DME. The lower olefin fraction (V) usually contains olefins of 2 to 4 carbon atoms and water.

In the olefin production means (7), the lower olefin fraction (V) is produced from the component (IV) containing methanol and DME, mainly through the following reaction.

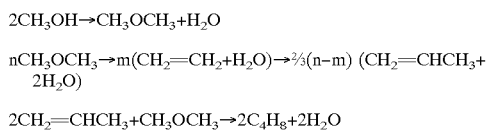

$2CH_3OH \rightarrow CH_3OCH_3 + H_2O$ $nCH_3OCH_3 \rightarrow m(CH_2=CH_2+H_2O) \rightarrow \frac{2}{3}(n-m)(CH_2=CHCH_3+2H_2O)$ $2CH_2=CHCH_3+CH_3OCH_3 \rightarrow 2C_4H_8+2H_2O$ As the catalyst employable in the olefin production means (7), a conventional catalyst for use in the production of lower olefins from methanol can be appropriately employed. For example, catalysts, such as SAPO-34, MFI and MFI type zeolite having been subjected to metallic ion exchange or substitution, can be preferably employed. Of these, a MFI type zeolite catalyst having been subjected to metallic ion exchange with Ca ion or Zn ion can be preferably employed as the MFI type zeolite having been subjected to metallic ion exchange or substitution.

The catalyst for the olefin production means (7) is desired to be periodically or continuously regenerated and used. The olefin production means (7) may be any of various types such as cyclic type, fluidized bed type and moving bed type.

The conditions for the reaction to produce the lower olefin fraction (V) from the component (IV) in the olefin production means (7) can be appropriately selected so that the ratio between the olefin components in the resulting lower olefin fraction (V) becomes a desired one. However, the pressure is desired to be in the range of usually about 0.5 to 8 $kg/cm^2$-G, preferably about 1 to 6 $kg/cm^2$-G, and the reaction temperature is desired to be in the range of usually about 300 to 700° C., preferably about 350 to 600° C.

When the lower olefins are produced from methanol, DME corresponds to an intermediate product of the reaction for producing the lower olefins from methanol, as indicated by the aforesaid chemical formulas. Therefore, the reaction to produce the lower olefin fraction (V) from the component (IV) containing DME and methanol in a specific ratio is higher in the reaction rate and of greater advantage than the production of lower olefins to form only methanol as a starting material. In the reaction of conversion from methanol into olefins, further, the quantity of exothermic heat due to the dehydration addition reaction of methanol is large, and hence it is necessary to remove the heat of the reaction. However, the reaction of conversion into olefins using DME as a starting material is advantageous because the quantity of exothermic heat due to the dehydration reaction is small and removal of the heat can be reduced. In the present invention, therefore, the amount of catalyst required for the olefin production can be held down, and the equipment cost related to the olefin production means (7) can also be reduced.

The lower olefin fraction (V) obtained through a line (22) from the olefin production means (7) as described above usually contains an ethylene fraction, a propylene fraction and a butene fraction. The weight ratio (ethylene/propylene) of ethylene to propylene can be a desired one but is usually controlled in the range of 0.7 to 1.6.

The lower olefin fraction (V) may be used as such, but it is preferable to introduce the fraction into a separation means (8) and to fractionate it into an ethylene fraction, a propylene fraction and a butene fraction by fractional distillation.

According to the process of the invention, a mixed fluid (I) containing DME and methanol in a specific ratio is used as a starting material, a liquid component (IV) containing DME and methanol in a specific ratio is obtained by partly separating and purifying the mixed fluid (I), then lower olefins are produced by the liquid component (IV). In this process, therefore, the reaction to synthesize an oxygen-containing compound and the reaction to produce lower olefins can be both carried out under milder conditions as compared with the process for producing lower olefins from methanol, and hence the energy and the equipment cost can be greatly reduced. According to the present invention, further, lower olefins containing ethylene and propylene in a desired ratio can be efficiently produced.

EXAMPLES

The present invention is further described with reference to the following examples based on simulation data and partly based on experimental data, but it should be construed that the invention is in no way limited to those examples.

Example 1

As shown in the flow sheet of FIG. 1, natural gas was introduced into a synthesis gas production means (1) through a line (11). Then, the synthesis gas obtained through a line (12) and recycle gas obtained through a line (16) were together pressurized and introduced into an oxygen-containing compound synthesis means (2) to obtain a mixed fluid (I) containing methanol and dimethyl ether through a line (13). The composition of the mixed fluid (I) is set forth in Table 1.

The mixed fluid (I) was then introduced into a high-pressure gas-liquid separation means (3) and separated into a gas component (II) and a liquid component (III) under the conditions of a temperature of 35° C. and a pressure of 110 $kg/cm^2$-G.

The gas component (II) was cooled to −40° C. by means of a condenser (4) and then subjected to gas-liquid separation using a gas-liquid separator (5) to obtain an off-gas through a line (18) and a liquid component through a line (19). The liquid component was allowed to join the liquid component (III) to obtain a liquid component (IV) present in a line (20). The compositions of the liquid component (III), the off-gas and the liquid component (IV) are set forth in Table 1.

Then, the liquid component (IV) was heated to 380° C. to be evaporated, and then introduced into an expander (6) at a pressure of 109 $kg/cm^2$-G. Then, the pressure of the liquid component (IV) was released to 6 $kg/cm^2$-G, and the pressure energy generated by the pressure release was recovered. The energy recovered in the pressure release was 32,000 kW.

The component (IV), the pressure of which had been released to 6 $kg/cm^2$-G, was introduced into an olefin production means (7) and converted into a lower olefin fraction (V). The energy recovered in the pressure release was used as a power of a compressor for recovering the later-described lower olefins obtained by the olefin production means (7). The resulting lower olefin fraction (V) was introduced into a fractional distillation means (8) to obtain fractions of ethylene, propylene and butene.

TABLE 1

| Composition | Mixed fluid (I) (ton/hr) | Liquid component (III) (ton/hr) | Off-gas (ton/hr) | Liquid component (IV) (ton/hr) |
| --- | --- | --- | --- | --- |
| $H_2$ | 320 | | 10 | |
| CO | 530 | | 20 | |
| $CO_2$ | 520 | 2 | 5 | 12 |
| $H_2O$ | 82 | 80 | | 80 |
| DME | 890 | 195 | 2 | 214 |
| MeOH | 120 | 105 | | 105 |

Example 2

A mixed liquid of methanol, DME and water in a weight ratio of 10/20/8 (methanol/DME/water) was used as a starting material. The mixed liquid was introduced into a tubular reactor (inner diameter: 10 mm, length: 600 mm) packed with 10 g of an extrusion molded product of SAPO-34 as a catalyst, and converted into lower olefins. The reaction in the tubular reactor was conducted under the conditions of a temperature of 500° C., a pressure of 1.5 kg/cm$^2$-G and GHSV of 3000 l/hr. The conversion ratio of methanol and dimethyl ether in the mixed liquid introduced into the tubular reactor was 99.6% by weight. The composition of the lower olefin fraction obtained from the tubular reactor is set forth in Table 2.

The mixed liquid used as a starting material in Example 2 had almost the same composition as that of the liquid component (IV) obtained in Example 1. Therefore, it was indicated by Example 2 that the liquid component (IV) obtained in Example 1 was favorably converted into a lower olefin fraction.

Example 3

A lower olefin fraction was obtained in the same manner as in Example 2, except that a mixed liquid of methanol, DME and water in a weight ratio of 10/10/4 (methanol/DME/water) was used as a starting material. The conversion ratio of methanol and dimethyl ether was 97.2% by weight. The composition of the resulting lower olefin fraction is set forth in Table 2.

Example 4

A lower olefin fraction was obtained in the same manner as in Example 2, except that a mixed liquid of methanol, DME and water in a weight ratio of 20/10/4 (methanol/DME/water) was used as a starting material. The conversion ratio of methanol and dimethyl ether was 95.8% by weight. The composition of the resulting lower olefin fraction is set forth in Table 2.

TABLE 2

|  | Ex. 2 | Ex. 3 | Ex. 4 |
|---|---|---|---|
| Components introduced into olefin production means MeOH/DME/H$_2$O (by weight) | 10/20/8 | 10/10/4 | 20/10/4 |
| Conversion ratio of MeOH and DME (wt %) | 99.6 | 97.2 | 95.8 |
| Composition of olefin fraction (wt %) |  |  |  |
| H$_2$—C$_1$ | 1.5 | 1.6 | 1.3 |
| C$_2$ | 0.7 | 0.9 | 1.1 |
| C$_2$= | 33.1 | 34.4 | 35.9 |
| C$_3$ | 2.2 | 2.9 | 2.7 |
| C$_3$= | 47 | 46.5 | 45.5 |
| C$_4$ | 6 | 5.3 | 5.0 |
| C$_4$= | 8.7 | 8.0 | 8.1 |
| C$_5$+— | 0.6 | 0.4 | 0.4 |
| Total | 100 | 100 | 100 |

What is claimed is:

1. A process for producing lower olefins, comprising the steps of:
    (A) separating a mixed fluid (I) obtained when a gaseous mixture containing carbon monoxide and hydrogen is introduced into an oxygen-containing compound synthesis means for reacting carbon monoxide and hydrogen with each other and synthesizing methanol, and from the methanol, forming dimethyl ether and water, said mixed fluid (I) containing carbon monoxide and hydrogen and dimethyl ether and methanol in a dimethyl ether/methanol weight ratio of 25/75 to 95/5 into a gas component (II) and a liquid component (III) by a high-pressure gas-liquid separation means under high pressure, wherein a part of the gas component (II) is introduced into the oxygen-containing compound synthesis means as a recycle gas, together with the gaseous mixture containing carbon monoxide and hydrogen, then separating the gas component (II) into an off-gas and dimethyl ether, and allowing the separated dimethyl ether to join the liquid component (III) to obtain a liquid component (IV) having a dimethyl ether/methanol weight ratio of 30/70 to 90/10, and
    (B) releasing the pressure of the liquid component (IV), and then introducing the liquid component (IV) into an olefin production means to form a lower olefin fraction (V) containing ethylene and propylene.

2. The process for producing lower olefins as claimed in claim 1, wherein the gaseous mixture containing carbon monoxide and hydrogen is a synthesis gas obtained from natural gas.

3. The process for producing lower olefins as claimed in claim 1, further comprising a step of fractionating the lower olefin fraction (V) into an ethylene fraction, a propylene fraction and a butene fraction by fractional distillation.

4. The process for producing lower olefins as claimed in claim 1, wherein the off-gas is used as a gas turbine fuel.

5. The process for producing lower olefins as claimed in claim 1, wherein energy generated by releasing the pressure of the liquid component (IV) is recovered in step (B).

6. The process for producing lower olefins as claimed in claim 5, wherein the energy generated by the pressure release is used to power a compressor.

7. The process for producing lower olefins as claimed in claim 1, wherein the dimethyl ether/methanol weight ratio in the liquid component (IV) is in the range of 40/60 to 80/20.

8. The process for producing lower olefins as claimed in claim 1, wherein a catalyst selected from the group consisting of SAPO-34, MFI, and MFI type zeolite having been subjected to metallic ion exchange or substitution is used in the olefin production means.

9. The process for producing lower olefins as claimed in claim 8, wherein a MFI type zeolite catalyst having been subjected to metallic ion exchange with Ca ion or Zn ion is used in the olefin production means.

10. The process for producing lower olefins as claimed in claim 1, wherein the catalyst is periodically or continuously regenerated and used in the olefin production means.

11. The process for producing lower olefins as claimed in claim 1, wherein the separation of the gas component (II) into an off-gas and dimethyl ether in the step (A) is any one selected from gas-liquid separation by cooling at a temperature of −60 to −20° C., separation using an inorganic membrane and separation using an organic membrane.

12. The process for producing lower olefins as claimed in claim 1, further comprising a step of fractionating the lower olefin fraction (V) into an ethylene fraction, a propylene fraction and a butene fraction by fractional distillation.

13. The process for producing lower olefins as claimed in claim 2, further comprising a step of fractionating the lower olefin fraction (V) into an ethylene fraction, a propylene fraction and a butene fraction by fractional distillation.

14. The process for producing lower olefins as claimed in claim 1, wherein the dimethyl ether/methanol weight ratio in the liquid component (IV) is in the range of 40/60 to 80/20.

15. The process for producing lower olefins as claimed in claim 2, wherein the dimethyl ether/methanol weight ratio in the liquid component (IV) is in the range of 40/60 to 80/20.

* * * * *